United States Patent [19]

Penaluna

[11] Patent Number: 4,608,146

[45] Date of Patent: Aug. 26, 1986

[54] HORIZONTAL ELECTROPHORESIS CELL FOR RAPID ASSEMBLY

[75] Inventor: William A. Penaluna, Pinole, Calif.

[73] Assignee: Bio-Rad Laboratories, Inc., Richmond, Calif.

[21] Appl. No.: 721,269

[22] Filed: Apr. 9, 1985

[51] Int. Cl.$^4$ ............................................. G01N 27/28
[52] U.S. Cl. ............................... 204/299 R; 204/182.8
[58] Field of Search ............. 204/299 R, 182.8, 182.7, 204/180 G

[56] References Cited

U.S. PATENT DOCUMENTS

| | | | |
|---|---|---|---|
| 3,902,987 | 9/1975 | Cawley | 204/299 R |
| 4,130,471 | 12/1978 | Grunbaum | 204/299 R X |
| 4,190,517 | 2/1980 | Monthony et al. | 204/182.7 X |
| 4,385,974 | 5/1983 | Shevitz | 204/299 R X |

*Primary Examiner*—John F. Niebling
*Assistant Examiner*—B. J. Boggs, Jr.
*Attorney, Agent, or Firm*—Townsend and Townsend

[57] ABSTRACT

An electrophoresis apparatus for use with horizontally disposed separation media is disclosed, comprised of a housing with lid, and removable components capable of applying an electric potential across a horizontally disposed medium, the components adapted for electrification by plugless electrical connections each of which establishes firm electrical contact with a power supply upon mere placement of the components in the housing. In its various embodiments, the apparatus is adapted to apply the potential through the use of electrified buffer solutions, electrified wires for placement in direct contact with the separation medium, or both. Spring-loaded contacts on either the buffer solution receptacles or the electrified wires mate with exposed power strips in the housing to form the connection. In the case of the electrified wires, the latter are mounted on a support to which spring-loaded braces are attached for compression by the lid of the housing when closed, such that even pressure is exerted by each wire against the separation medium along the full length of contact, regardless of the position of the separation medium in the housing.

30 Claims, 8 Drawing Figures

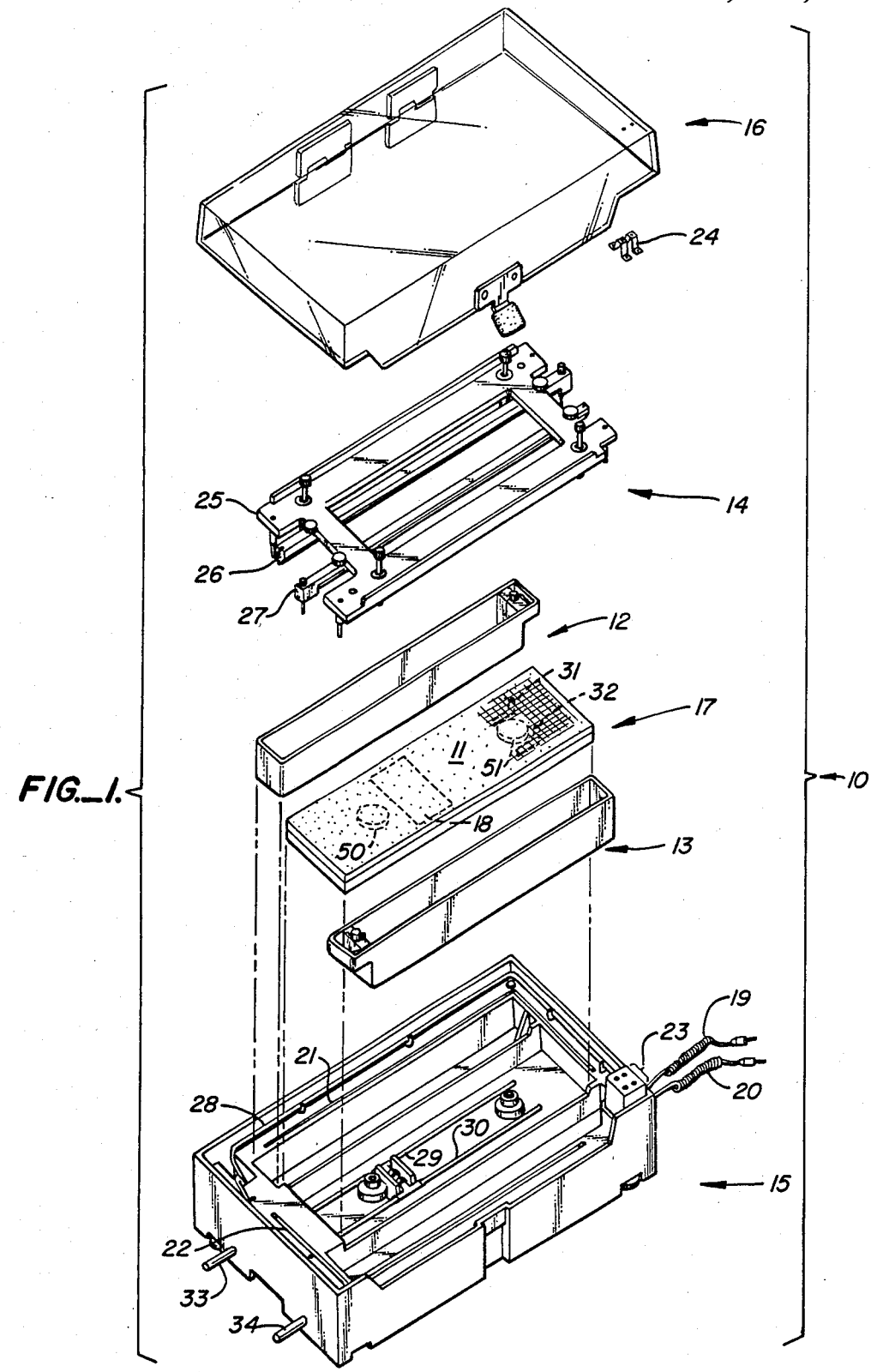

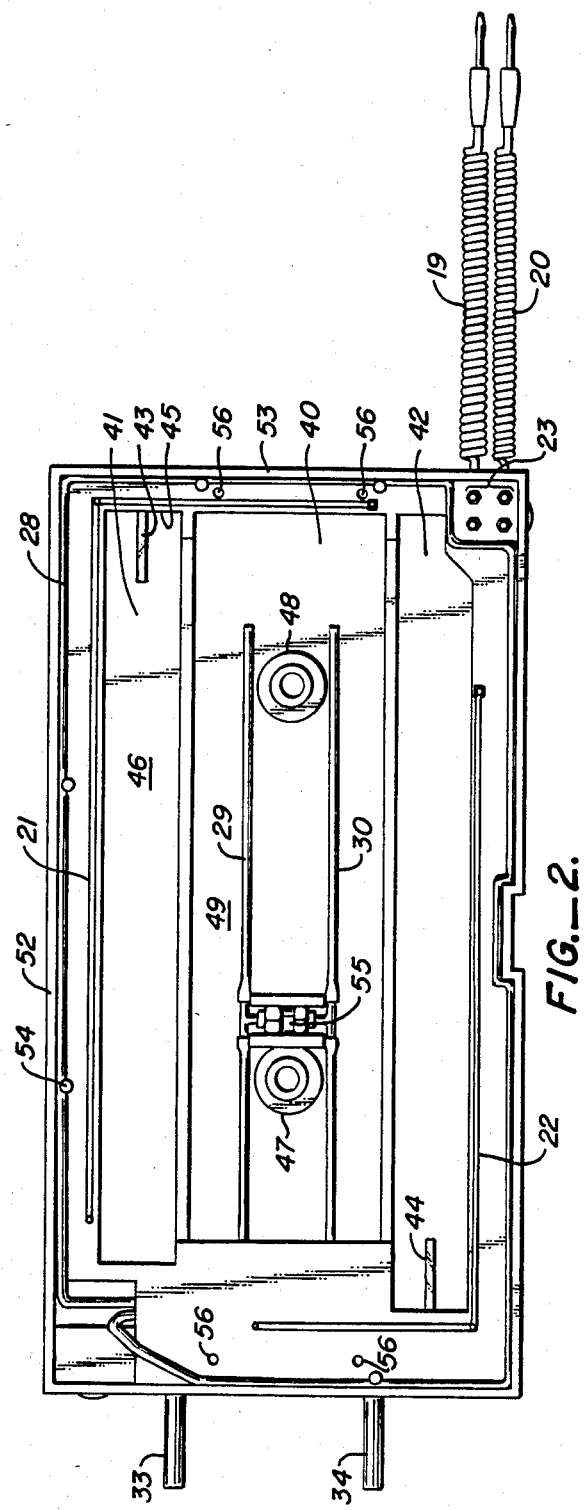
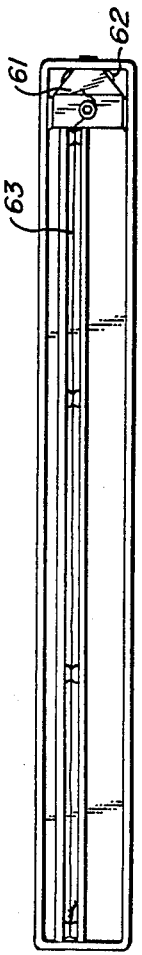
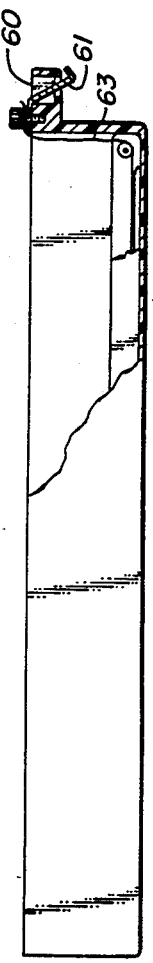
FIG.—2.
FIG.—3a.
FIG.—3b.

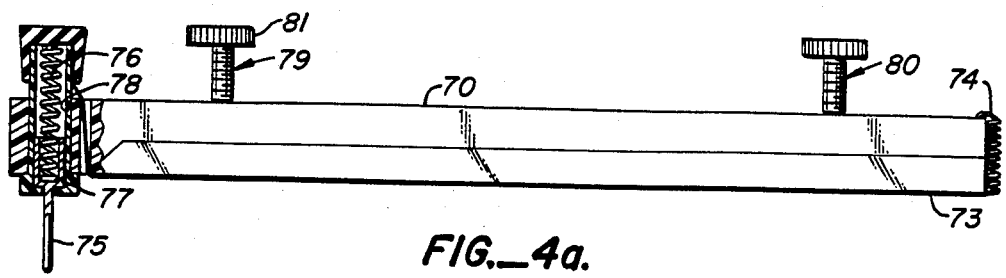
FIG._4a.
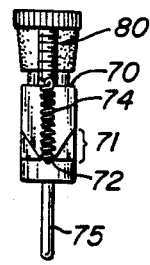
FIG._4b.
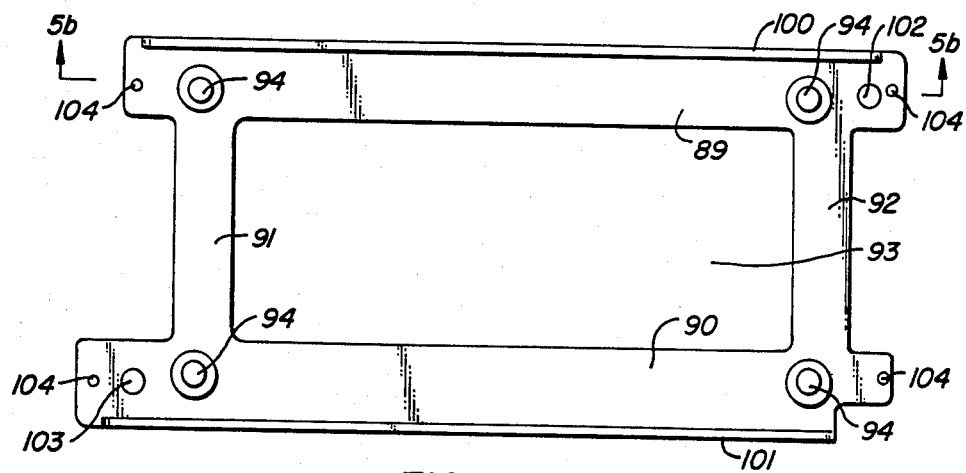
FIG._5a.
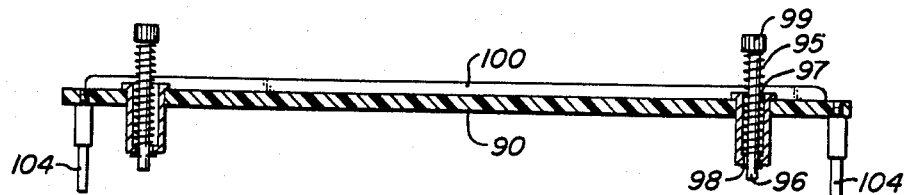
FIG._5b.

HORIZONTAL ELECTROPHORESIS CELL FOR RAPID ASSEMBLY

BACKGROUND OF THE INVENTION

This invention relates to apparatus for horizontal electrophoresis and related techniques involving the application of an electric potential along a horizontally oriented medium. The term "electrophoresis" will be used herein to encompass all such techniques, including the simple unidirectional application of an electric field across a stationary medium such as a gel, and all other separation techniques in which an electric field is used.

Of the various methods of performing electrophoresis, horizontal electrophoresis has the advantage of permitting the use of an open-faced separation medium. The medium may be a thin coating on a slide or a beaded aggregate in a shallow bed, and frequently rests on a cooling plate which removes the heat generated by the electric current. An electric potential is applied across the medium either through buffer solutions located adjacent to opposite side edges of the surface and held in electrical connection with the medium by the use of saturated wicks, or bare electric leads placed in direct contact with the medium along opposing side edges.

Assembly of the structure, particularly inserting the medium and then making all necessary electrical connections to apply the potential, is problematic in existing devices. Some of the problems are the awkwardness of plugging the various contacts into one another, the delicacy of the separation medium and the need to avoid disturbing it during assembly of the apparatus, and the need to accommodate a variety of types, shapes and sizes of separation media. Imperfect electrical connections have also been a problem, particularly when the delicacy of the separation medium requires careful handling.

Accordingly, for the safety of the operators of the equipment, the reliability of the equipment performance, and the ability to rapidly assemble and disassemble the equipment, a device overcoming these problems and possibly others encountered in connection with the existing equipment is presented herewith.

SUMMARY OF THE INVENTION

A novel horizontal electrophoresis apparatus consisting of a housing and removable parts is provided, the apparatus characterized by plugless electrical connections which make firm electrical contacts upon mere placement of the parts in the housing. The invention extends to two types of apparatus for applying an electrical potential across a horizontal separation medium —i.e., apparatus in which the medium is placed in contact with electrified buffer solutions, and apparatus in which the medium is contacted directly with electrified metallic leads.

In each case, a spring-loaded electrical contact forms the connection between the housing and removable parts associated with it. The spring-loaded contact extends from either the liquid receptacle which contains buffer solution or the electrified leads, and the connection is made by compression of the contact against an exposed conductor in the housing. In the preferred arrangement, the spring-loaded contacts extend downward, while the conductors are exposed for access from above. Proper contact is achieved by upward compression of the spring resulting from the force of gravity on either the liquid receptacle in the case of buffer solutions or an electric lead support in the case of bare leads in direct contact with the medium.

In the case of the electrified leads, a further feature of the invention are spring-loaded braces associated with the leads, causing the leads to apply substantially equal pressure to the medium along the full contact length. The braces are compressed between a support on which the leads are mounted and a lid which encloses the housing. As a result, the leads press evenly across the full width of the medium when the lid is closed, regardless of the location of the medium relative to the center of gravity of the support. This is particulary useful where narrow media are used, avoiding the need to center such media inside the apparatus.

The invention is thus applicable to both types of apparatus, i.e., that utilizing buffer solutions and that utilizing bare electric leads in direct contact with the medium. In its preferred embodiments, the invention is incorporated in an apparatus having a single housing adapted to accommodate both types of electrical contact for alternative use. The overall result in any case is an apparatus capable of quick, easy and essentially mistake-proof assembly and disassembly of parts and electrical connections. Use of the inventive concepts herein further leads to a versatile apparatus having a wide range of adaptability to horizontal electrophoresis media of various configurations, sizes and physical and chemical natures.

In various preferred embodiments involving the use of bare electric leads, the spacing of the leads, their orientation in the housing or both, are adjustable to accommodate separation media of a wide range of widths and lengths, as well as several media at once. Accordingly, the leads in such embodiments are mounted on supports which are attachable to a frame by fasteners which can attach to any point along the rails of the frame. Preferred frames have both longitudinal and transverse rails, each of which are capable of receiving the fasteners at any location along their lengths.

Further contributing to the wide range of size adaptability are the exposed conductors in the housing. These are preferably elongate strips extending along opposite sides of the surface supporting the separation medium. Particularly preferred strips are those which extend from diagonally opposed corners of the support surface upon which the medium rests, particularly when the surface is rectangular. Each strip may thus extend in two directions from its respective corner, the two conductors thus forming a pair of L-shaped strips, facing each other and surrounding the surface.

Other features, functions, variations and embodiments within the scope of the present invention will become apparent upon reference to the attached drawings and the description which follows.

BRIEF DESCRIPTION OF THE DRAWINGS

FIG. 1 is an exploded perspective view of a full equipment assembly forming an illustrative embodiment of the present invention, including as structures normally contemplated for alternative use a pair of buffer solution receptacles as well as a support for bare electric leads.

FIG. 2 is a top plan view of one of the components of the embodiment shown in FIG. 1, i.e., the base portion of the housing thereof.

FIGS. 3a and 3b are longitudinal side views of one of the buffer solution receptacles of the embodiment of FIG. 1, shown in partial cutaway.

FIGS. 4a and 4b are a longitudinal side elevation and a transverse side elevation, respectively, of one of the mounts of the embodiment of FIG. 1 for holding the bare electric leads.

FIGS. 5a and 5b are a top plan view and a longitudinal side section, respectively, the latter taken through line B—B of the former, of the frame shown in FIG. 1 for supporting the electric lead mounts.

DETAILED DESCRIPTION OF THE PREFERRED EMBODIMENTS

The various parts which together constitute a horizontal electrophoresis apparatus 10 forming one embodiment of the present invention are shown in FIG. 1 in exploded form. These parts include a surface 11 for supporting the separation medium; alternative components for applying an electric potential across a medium placed on the surface 11, i.e., buffer solution receptacles 12 and 13 for placement on opposite sides of the surface as one alternative, and a support 14 for the exposed electric leads for placement above the surface as the other alternative; and a housing including a base 15 capable of receiving the above-mentioned components and a lid 16 capable of enclosing the base 15.

The separation medium support surface 11 in this embodiment is the upper surface of a removable block 17. The block is preferably hollow with an internal serpentine passage for coolant circulation. Accordingly, the upper surface 11 may be fabricated from a high heat conductivity material promoting the removal of heat generated in the separation medium by the electric current passing through the medium. Although curved surfaces may be used, the preferred surfaces are flat as in the embodiment shown in the drawing.

The surface supports any of a variety of separation media, including gels, slurries, suspensions, and any fluid-containing medium through which a charged species can migrate under the influence of an electric field. The medium may extend over the entire surface or a portion thereof. In the drawing, a rectangularly shaped medium 18, shown in dashed lines, covers a portion of the surface. A typical such medium is a gel, and several such gels may be placed side by side on the surface for simultaneous electrophoresis.

Extending from the exterior of the base 15 are a pair of insulated leads 19 and 20 for connection to an external power supply. Exposed conductors 21 and 22 are affixed to the interior of the base 15. The conductors are shown here as elongated strips with extended flat surfaces which supply power to the buffer solution receptacles 12, 13 or the exposed electric lead support 14 upon simple contact. Each conductor strip is connected through electric lines (not shown) within the enclosed walls of the base 15 to the first of a pair of terminals 23 extending upward from the base, the second terminal in each pair being similarly connected to one of the external insulated leads 19, 20 through internal connections (also not shown). The gap between the terminals in each pair is bridged by the jumper 24 inside the lid 16 of the housing when the lid is closed. The circuit is those closed only when the lid is lowered. This is a safety measure, preventing the operator from accidentally touching electrified buffer solutions or conductor strips when the lid is raised.

In the embodiment shown in these drawings, the buffer solution receptacles 12, 13 are open troughs extending the full length of the surface 11 which supports the separation medium. Accordingly, the receptacles are intended for placement on either side of the surface. Fluid contact between the buffer solutions and the separation medium 18 (generally a gel when buffer solutions are used) resting on the surface 11 is achieved in a conventional manner, typically by the use of paper wicks (not shown) extending from the interior of each trough 12, 13 up to the nearest edge of the gel 11. The surface forces of a liquid saturating the wick serve to hold it in place against the gel. A description and drawing of one example of such a wick arrangement is found in Monthony, et al., U.S. Pat. No. 4,190,517, Feb. 26, 1980, incorporated herein by reference.

The electric lead support in this embodiment is a frame 25 with detachable mounts 26 and 27, one for each lead. The leads, which may be strips or wires, the latter being preferred, although not visible in the view shown in FIG. 1, are extended in parallel straight lines the length of each mount, exposing the leads downward for access to the separation media resting on the support surface 11. In the arrangement shown, the detachable mounts 26, 27 are fastened in the longitudinal direction to place the leads in contact with the gel 18 at locations close to the side edges of the gel when the frame 25 is lowered into place. The mounts may also be secured on the frame in the direction perpendicular to that shown to apply a potential in the longitudinal direction of the support surface 11, for use with large gels or to permit two-dimensional electrophoresis without moving the gel.

A further feature shown in FIG. 1 is a peripheral condenser coil 28, in the form of a tube extending around the perimeter of the inside of the base. When coolant is circulated through this tube, moisture in the atmosphere above the separation medium is drawn laterally toward the tube, thus preventing condensation on the lid 16 of the apparatus, which might hinder the visual observation of the support medium during electrophoresis (when the lid is of transparent material) as well as interfere with the medium by dripping fluid thereon. The condenser coil 28 may be secured to the inside of the base 15 as shown or to the inside of the lid 16 as disclosed in Monthony, et al., supra. The arrangement shown in FIG. 1 is preferred. Coolant passing through the condenser coil 28 also passes through open tubes 29 and 30 along the floor of the interior of the base 15, for connection to inlet and outlet ports 31, 32 on the underside of the separation medium cooling block 17. External connections 33, 34 extend from the base 15 for attachment of supply lines from a coolant source (not shown).

Turning now to FIG. 2, a top plan view of the housing base 15 of the embodiment of FIG. 1 is shown. The base contains a compartment 40 for the coolant block supporting the separation medium, plus compartments 41, 42 for the buffer troughs. The trough compartments are longer than the troughs themselves, and each contains an obstruction 43, 44 on the inside at one end, as an orientation guide for placement of the troughs in opposite directions. The spring-loaded contacts extending from the troughs, described in detail hereinbelow, will then be directed toward opposite ends of the base. The obstructions, which are also visible in the perspective view in FIG. 1, are shown in the form of angled protrusions extending from the end wall 45 of the respective compartment down to the floor 46 of the compartment.

The support block compartment 40, located in the center of the base, contains a pair of bosses 47, 48 extending upward from the floor 49 of the compartment. The bosses mate with similarly shaped indentations 50, 51 in the bottom of the block, indicated in dashed lines in FIG. 1, to immobilize the block in the compartment. The bosses may be hollow to receive threaded securing bolts (not shown), whose threads mate with internal threads in the indentations 50, 51 to more securely immobilize the block during handling and transport of the apparatus.

In this embodiment, the exposed conductors 21, 22 which supply current to both the buffer solutions and the bare leads used for direct contact are elongate, flat power strips. Each strip extends along one side wall 52 and one end wall 53 of the housing base, joined at the corner to form a continuous L-shaped contact surface. As shown, there is one such power strip for each polarity, the strips being electrically insulated from each other. As indicated in the discussion relating to FIG. 1, each strip is connected through a pair of exposed terminals 23 to exterior leads 19, 20 for connection to a power supply, the terminals in each pair 23 being bridged by a separate jumper 24 (FIG. 1) when the lid 16 is closed. Shaped in this manner, the power strips are capable of supplying power to either the buffer tanks or the direct contact leads, and indeed with the leads placed at any location along the entire length or width of the cell in either the longitudinal or transverse direction. The means by which electrical contact between the power strips on the one hand and both the buffer tanks and the direct contact leads on the other is achieved is shown in the subsequent figures and described in detail hereinbelow.

As further seen in the top plan view of FIG. 2, the condenser tubing 28 runs along the side surfaces of the end walls 52 and side walls 53 of the housing base, held in place by pegs 54. The coolant tubes 29, 30 extending into the central compartment 40 for connection to the separation medium support block form a common circulation path with the peripheral portion of the coil 28. The passages in the support block itself complete the coolant circuit when the block is inserted in the compartment 40. A safety valve 55 is incorporated into the coolant circuit to permit bypass of the coolant in the event of a pressure surge in the coolant supply, thus avoiding inadvertent damage to the support block or opening of the connections between the support block and the coolant tubes 29, 30 feeding it.

The loop portion 28 of the cooling tube is positioned to draw evaporated moisture away from the region above the separation medium to avoid the dripping of condensation into the medium, in accordance with the disclosure of Monthony, et al., supra. In the embodiment shown, the loop is further sufficiently removed from both the buffer tank compartments 41, 42 and the power strips 21, 22 to avoid dilution of the former and interference with the latter. A shallow trench (not shown) may be formed in the surface of the base following the path of and immediately underneath the loop, to contain any condensation dripping from the loop.

One buffer solution receptacle is shown in detail in the side elevation partial cutaway view of FIG. 3. This receptacle is an elongate rectangular trough, open at the top, with a projection 60 extending longitudinally from one end. Mounted on the projection is a spring-loaded electrical contact 61 positioned to compress against one of the exposed conductors 21, 22 in the base when the trough is placed in the appropriate compartment 41, 42 (see FIG. 1). The contact in this embodiment is a resilient metallic tab extending downward through a slot 62 in the tank projection 60 at an angle, the slot providing sufficient clearance to permit upward deflection of the tab by the conductor strip.

Extending from the tab into the interior of the tank itself is an exposed electric wire 63. This wire extends the full length of the tank.

Returning once again to FIG. 1, it can be seen that the electric lead support designed to place bare leads in direct contact with the separation medium consists of a frame 25 and detachable mounts 26 and 27. One such mount is shown in detail in FIGS. 4a and 4b in a side and end view, respectively. The mount is comprised of an elongate beam 70 of nonconductive material. The cross-section of the beam, as evident from FIG. 4b, contains a section 71 which tapers downward to a long narrow surface 72 extending almost the entire length of the beam. Extending along the length of this surface is the electric lead 73, which is preferably a wire of circular cross-section. The wire is unshielded and will accordingly be in electrical contact with the separation medium over which the beam is placed. The wire is maintained under tension by a spring-loaded anchor, shown in this embodiment as a coil spring 74, at one end of the beam.

A spring-loaded electrical contact is located at the other end of the beam. Its components include a rod-shaped projection 75 and a coil spring 76 which fits into a cup-shaped extension 77 on one end of the projection. The spring 76 and the rod-shaped projection 75 are permitted vertical movement inside a passage 78 extending through the end of the beam 70. The wire 73 running along the bottom of the beam is passed upward through the beam adjacent to the through passage 78 and is secured to the upper end of the coil spring 76, forming an electrical contact down through the tip of the rod 75. The spring-loaded rod 75 is of sufficient length to contact one of the exposed conductors 21, 22 in the housing when the wire 73 is placed in contact with the separation medium.

The beam 70 is further equipped with a pair of compression fasteners 79, 80 for securing the beam to the frame (described below). Each of these fasteners is a screw with a broad flat head 81 having a knurled or ridged rim permitting turning of the screw by hand. The screws are positioned such that opposing rails of the frame will fit between the screw head 81 and the upper surface of the beam 70. The beam is then secured in place by tightening the screws.

The frame to which the beams are secured is shown in FIGS. 5a and 5b in top plan and side section views, respectively. The frame consists of a pair of parallel longitudinal rails 89, 90 joined by a pair of parallel transverse rails 91, 92. The rails define a central open space 93 which permits visual observation of the separation medium during electrophoresis. The rails in this embodiment are flat strips of rigid material, permitting attachment of the electric lead mounts at any location along their length.

The spacing of the rails corresponds to the spacing of the compression fasteners 79, 80 on the electric lead mounts. The spacings may be selected such that the fasteners on a single mount will secure to the inside edges of opposing rails, or the outside edges, or one inside and one outside. Accordingly, the spacing between the longitudinal rails 89, 90 may be equal to or different than that between transverse rails 91, 92, although intended for use with the same pair of compression fasteners.

In the preferred embodiment, however, as shown in FIG. 5a, the spacing between the longitudinal rails is narrower than that between the transverse rails. It is further preferred that a second, shorter pair of electric lead mounts be used when the leads are extended transversely across the frame. Thus, the components of the apparatus may include a single frame and two pairs of mounting beams for securing thereto, a short pair for transverse mounting and a long pair for longitudinal mounting.

The frame further contains at least one pair of spring-loaded braces 94 to provide compressive tension between the frame and the lid of the apparatus when the lid is closed. This evens out the pressure which the frame and the electric lead mounts attached thereto exert on the medium resting on the support surface. The balancing of pressure serves to ensure even, continuous electrical contact along the full length of the edge of the medium. This is a particularly useful result when the medium is placed off-center on the support surface. When the center of gravity of the frame does not overlap with the boundaries of the medium, the frame would otherwise have a tendency to tilt due to its own weight. The braces thus serve as a leveling device.

When the frame is designed for the fastening of the electric lead mounts in only one direction, two such braces will suffice, provided that they are spaced apart from each other in the direction parallel to the electric lead mounts. In the preferred construction, as shown in the Figure, four such braces are included, one at each corner of the frame, thus providing even, balanced contact of the leads regardless of whether the medium is off-center longitudinally or transversely.

As shown in FIG. 5b, each brace may be constructed of a captive coil spring 95 encircling a movable rod 96 which passes through a hole 97 in the frame. A retaining ring 98 fixed to the lower end of the rod 96 limits the range of motion of the rod. A blunt upper end 99 extends upward from the rod to contact the housing lid, which pushes the rod downward, compressing the coil spring 95.

Further features of the frame include reinforcing ribs 100, 101 to impart rigidity to the structure, colored indicator disks 102, 103 indicating positive and negative polarities as guides for insertion of the frame into the housing, and guide pins 104 which mate with similarly placed apertures 56 in the housing base (see FIG. 2), again to ensure proper placement of the frame inside the housing.

Additional components not shown in the drawing although required for typical laboratory use of the apparatus include a DC power supply and a source of coolant fluid such as cold water.

The materials of construction are not critical. In general, any rigid nonconducting material may be used, preferably inert to any of the chemicals used in the separation media or buffer solutions. A transparent lid enables one to monitor the apparatus while it is in use.

The foregoing description is offered for illustrative purposes only. Numerous modifications, variations and further embodiments beyond those described herein will be readily apparent to those skilled in the art, while still falling within the spirit and scope of the invention as claimed hereinbelow.

What is claimed is:

1. In an apparatus for electrophoresis across a horizontally disposed separation medium, said apparatus including a support surface capable of supporting said separation medium and having an opposing pair of side edges and an opposing pair of end edges, a pair of open receptacles capable of retaining buffer solutions, and a housing capable of retaining said support surface and one of said receptacles along each of said side edges, said housing having positive and negative terminals adapted for connection to a power supply, the improvement comprising:

a pair of first electrical contacts in said housing electrically connected to said positive and negative terminals, respectively; and a pair of exposed leads, one said lead inside each said receptacle, said leads electrically connected to a pair of second electrical contacts respectively;

one of said first and second pairs of electrical contacts being spring-loaded and adapted to compress against the other of said first and second pairs of electrical contacts when said receptacles are placed in said housing.

2. Apparatus according to claim 1 in which said first electrical contacts are spring-loaded and adapted to compress against said second electrical contacts when said receptacles are placed in said housing.

3. Apparatus according to claim 1 in which said open receptacles are troughs each extending the full length of one of said side edges, and one of said second electrical contacts is secured to one end of each said trough respectively.

4. Apparatus according to claim 1 in which said open receptacles are troughs each extending the full length of one of said side edges, said exposed leads are electric wires extending substantially the full length of each said trough, and one of said second electrical contacts is secured to one end of each said trough respectively.

5. Apparatus according to claim 1 in which said first electrical contacts are substantially flat, each having an exposed area at least as large as the area of the second electrical contact compressing against it when said receptacle is placed in said housing.

6. Apparatus according to claim 1 in which said first electrical contacts are exposed upward and said second electrical contacts are spring-loaded and exposed downward for compression by said first electrical contacts by gravitational force exerted on said receptacles.

7. Apparatus according to claim 6 in which each said second electrical contact is a resilient inclined tab extending downward from one of said receptacles.

8. Apparatus according to claim 1 in which said first electrical contacts are disposed adjacent to opposite edges respectively of said support surface.

9. Apparatus according to claim 1 in which said first electrical contacts are disposed adjacent to opposite end edges respectively of said support surface.

10. Apparatus according to claim 1 in which said housing is substantially rectangular having an opposing pair of end walls and an opposing pair of side walls, and said first electrical contacts are elongate flat conductor strips extending from diagonally opposed corners of said housing along said end walls.

11. In an apparatus for electrophoresis across a horizontally disposed separation medium, said apparatus including a support surface capable of supporting said separation medium and having an opposing pair of side edges and an opposing pair of end edges, a pair of troughs capable of retaining buffer solutions, each said trough extending the full length of one of said side edges, and a housing capable of retaining said support surface and said troughs with one said trough along each of said side edges, said housing having positive and negative terminals adapted for connection to a power supply, the improvement comprising:

a pair of substantially flat electrical contacts in said housing exposed upward and disposed adjacent to opposite end edges respectively of said support surface, said contacts electrically connected to said positive and negative terminals, respectively; and an exposed electric wire inside each said trough extending substantially the full length thereof, each said electric wire electrically connected to a resilient inclined tab of electrically conductive material extending downward from one end of each said trough respectively to compress against one of said flat electrical contacts when said receptacle is placed in said housing.

12. In an apparatus for electrophoresis across a horizontally disposed separation medium, said apparatus including a support surface capable of supporting said separation medium, a pair of elongate exposed electric leads, a housing including a base capable of retaining said support surface and said electric leads and a lid adapted to enclose said base, said housing having positive and negative terminals adapted for connection to a power supply, the improvement comprising:

a pair of exposed conductors electrically connected to said positive and negative terminals respectively and disposed alongside said gel support surface;

an electric lead support exposing each said lead to said support surface in substantially parallel stright lines, said support having a spring-loaded electrical contact electrically connected to each said lead, each said contact adapted to compress against one of said exposed conductors when said electric lead support rests on said gel support surface; and at least one pair of spring-loaded braces spaced apart from each other in the direction of said parallel straight lines, each said brace adapted for compression between said electric lead support and said lid when said lid is closed.

13. Apparatus according to claim 12 in which said support surface is substantially rectangular with an opposing pair of side edges and an opposing pair of end edges, and said electric lead support extends said electric leads parallel to said side edges and substantially the full length thereof.

14. Apparatus according to claim 12 in which said support surface is substantially rectangular with an opposing pair of side edges and an opposing pair of end edges, said electric lead support is capable of extending said electric leads parallel to either said side edges or said end edges, and said apparatus includes two said pairs of spring-loaded braces, one said brace adjacent to each corner of said support surface.

15. Apparatus according to claim 12 in which said electric lead support comprises:

a pair of mounts, each having affixed thereto one said spring-loaded electrical contact and one said exposed lead electrically connected to said contact, and a frame containing at least one rail capable of having said pair of mounts affixed thereto with said leads parallel.

16. Apparatus according to claim 12 in which said electric lead support comprises:

a pair of mounts, each having affixed thereto one said spring-loaded electrical contact and one said exposed lead electrically connected to said contact, and a frame containing at least one rail capable of having said pair of mounts affixed thereto at any point along the length thereof with said leads parallel to each other and perpendicular to said rail;

and said exposed conductors are elongate strips running parallel to said rail on opposite sides of said support surface.

17. Apparatus according to claim 16 in which each said mount contains at least one compression fastener capable of rigidly securing said mount to said rail at any point along the length thereof.

18. Apparatus according to claim 12 in which said electric lead support comprises:

a pair of mounts, each having affixed thereto one said spring-loaded electrical contact and one said exposed lead electrically connected to said contact, and a frame containing at least one transverse rail and at least one longitudinal rail, each said rail capable of having said pair of mounts affixed thereto at any point along the length thereof with said leads parallel to each other and perpendicular to said rail, and said spring-loaded electrical contacts at opposite ends;

said support surface is substantially rectangular; and each said exposed conductor is comprised of two elongate strips along adjacent sides of said support surface, joined at the corner.

19. Apparatus according to claim 18 in which said frame contains two said transverse rails and two said longitudinal rails defining a central open space permitting visual observation therethrough.

20. Apparatus according to claim 18 in which said frame contains two said transverse rails and two said longitudinal rails defining a central open space permitting visual observation therethrough, and each said mount contains two compression fasteners spaced apart from each other to secure said mount to either said two transverse rails simultaneously or said two longitudinal rails simultaneously.

21. Apparatus according to claim 18 in which each said mount is a substantially straight beam with said exposed lead secured along the exterior and extending the length thereof and said spring-loaded electrical contact affixed to one end thereof, the cross-section of said beam tapering toward said exposed lead.

22. Apparatus according to claim 12 in which said electric lead support further contains a plurality of guide pins extending downward therefrom, and said housing contains an aperture to receive each said guide pin thereby securing said electric lead support inside said housing in accordance with a preselected orientation.

23. Apparatus according to claim 12 in which each said electric lead is secured to said electric lead support by a spring-loaded anchor which maintains said lead under tension.

24. Apparatus according to claim 12 in which said exposed conductors are secured to the interior of said housing and exposed upward, and said spring-loaded electrical contacts extend downward from said electric lead support.

25. Apparatus according to claim 12 in which said spring-loaded braces are affixed to said electric lead support.

26. Apparatus according to claim 12 comprising two pairs of said spring-loaded braces affixed to said electric lead support in a substantially rectangular arrangement.

27. Apparatus according to claim 12 in which said electric lead support is substantially rectangular, and said apparatus contains two pairs of said spring-loaded braces, one said spring-loaded brace mounted to each of the four corners of said electric lead support.

28. In an apparatus for electrophoresis across a horizontally disposed separation medium, said apparatus including a substantially rectangular support surface capable of supporting said separation medium, a pair of elongate exposed electric leads, a substantially rectangular housing including a base capable of retaining said support surface and said electric leads and a lid adapted to enclose said base, said base having positive and negative terminals adapted for connection to a power supply, the improvement comprising:

a pair of exposed conductors in said base, electrically connected to said positive and negative terminals respectively, each said conductor comprising two elongate strips along adjacent side walls of said base and joined at the corner;

at least one pair of elongate electric lead mounts, each said mount having affixed thereto one said exposed electric lead extended into a straight line and one spring-loaded electrical contact at one end of said mount and electrically connected to said exposed lead;

a substantially rectangular frame containing two transverse rails and two longitudinal rails defining a central open space;

a pair of compression fasteners on each said electric lead mount, capable of simultaneous attachment to either said transverse rails or said longitudinal rails at any point along the length thereof;

four spring-loaded braces extending upward from said frame, one said brace at each of the four corners thereof, adapted for compression by said lid when said lid is closed.

29. In an apparatus for electrophoresis across a horizontally disposed separation medium, said apparatus including a support surface capable of supporting said separation medium, positive and negative terminals connected to a power supply, and a lid, said apparatus being adapted to provide electrical contact between a separation medium on said support surface and both a pair of buffer solutions retained in open receptacles and a pair of first elongate exposed electric leads as alternative means of applying an electric potential across said separation medium, the improvement comprising:

a pair of exposed conductors electrically connected to said positive and negative terminals respectively and disposed alongside said support surface;

a second exposed electric lead inside each said receptacle, each said second lead electrically connected to a first spring-loaded electrical contact adapted to compress against one of said exposed conductors when said receptacle is placed alongside said support surface;

an electric lead support, exposing each said first electric lead to said support surface in substantially parallel straight lines, said electric lead support having a second spring-loaded electrical contact electrically connected to each said first electric lead, each said second contact adapted to compress against one of said exposed conductors when said electric lead support rests on said support surface; and at least one pair of spring-loaded braces spaced apart from each other in the direction of said parallel straight lines, each said brace adapted for compression between said electric lead support and said lid when said lid is closed.

30. In an apparatus for electrophoresis across a horizontally disposed separation medium, said apparatus including a substantially rectangular block capable of supporting said separation medium; a pair of troughs capable of retaining buffer solutions, each said trough having an exposed electric wire disposed therein for immersion in said buffer solution; a pair of elongate electric leads mounted on a support in substantially parallel straight lines; a substantially rectangular base sized to retain said block and either said pair of troughs or said support, said base containing positive and negative terminals adapted for connection to a power supply; and a lid capable of enclosing said base; the improvement in which:

said base contains a pair of exposed conductors mounted therein and exposed upward, said conductors electrically connected to said positive and negative terminals respectively, each said conductor comprising two elongate strips along adjacent walls of said base and joined at the corner, said corners being diagonally opposed across said base;

each said trough has affixed thereto a first spring-loaded contact extending downward from one end thereof and electrically connected to said exposed electric wire therein;

said support comprises two transverse rails and two longitudinal rails joined to form a substantially rectangular frame, with a spring-loaded brace extending upward from each corner thereof for compression by said lid when said lid is closed; and at least one pair of mounting beams to which said elongate electric leads are mounted, each said beam having a second spring-loaded contact extending downward from one end thereof and electrically connected to the elongate electric lead mounted thereto, and a pair of compression fasteners capable of simultaneous attachment to either said transverse rails or said longitudinal rails at any point along the length thereof.

* * * * *